US006566371B2

(12) United States Patent
Jackson (10) Patent No.: US 6,566,371 B2
(45) Date of Patent: May 20, 2003

(54) INTRAPERITONEAL ADMINISTRATION OF ADENOSINE FOR THE TREATMENT OF PREVENTION OF GASTROINTESTINAL OF SYSTEMIC DISEASES (75) Inventor: Edwin K. Jackson, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/844,255

(22) Filed: Apr. 30, 2001

(65) Prior Publication Data

US 2002/0013290 A1 Jan. 31, 2002

Related U.S. Application Data (60) Provisional application No. 60/200,360, filed on Apr. 28, 2000.

(51) Int. Cl.[7] .............................................. A61K 31/52
(52) U.S. Cl. ........................ 514/310; 514/262; 514/265
(58) Field of Search ................................ 514/266, 262, 514/265

(56) References Cited

U.S. PATENT DOCUMENTS 4,994,442 A  *  2/1991  Gil et al.
5,902,793 A     5/1999  Bloom et al.

OTHER PUBLICATIONS

Jackson, E.K., et al., *Aliment Pharmacol Ther.* 14: 1371–1380 (2000).
Dignass et al., Adenosine nucleotides modulate epithelial wound healing in vitro, abstract, Jul. 1998.*
Proctor, K.G., *Circulation Res.* 59: 474 (1986).
Proctor, K.G., *Circulation Res.* 61: 187 (1987).
Jackson, E.K., *Am. J. Physiol.* 253: H909 (1987).
Kuan, C.J., et al., *Am. J. Physiol.* 255: H386 (1988).
Holycross, B.J., et al., *J. Pharmacol. Exp. Ther.* 250: 433 (1989).
Dawicki, D.D., et al., *Thromb. Res.* 43:161 (1986).
Paul, S., et al., *J. Pharmacol. Exp. Ther.* 267: 838 (1993);.
Cristalli, G. et al., *Naunyn–Schmiedebergs Archives of Pharmacology* 349: 644 (1994).
Cronstein, B.N., *J. App. Physiol.* 76:5 (1994).
Revan, S., et al., *J. Biol. Chem.* 271: 17114 (1996).
Jordan, J.E., *J. Pharmacol. Exp. Ther.* 280:301 (1997).
Kaminski, P.M., et al., *Circulation Res.* 65: 426 (1989).
Kaminski, P.M., et al., *Circulation Res.* 71:720 (1992).
Wagner, D.R., et al., *Circulation* 97: 521 (1998).
Cain, B.S., et al., *J. Surg.. Res.* 76:117 (1998).
Dubey, R.K., et al., *Circulation* 96:2656 (1997).
Dubey, R.K., et al., *Hypertension* 31:943 (1998).
Klein, E.S., et al.,*J. Surg. Res.* 61: 473 (1996).
Thompson, J., *Digest. Surg.* 15:153 (1998).
Jarvis, S.M., et al., *Biochem. J.* 208: 83 (1982).
Mi, Z., et al., *J. Pharmacol. Exp. Ther.* 287: 926 (1998).
Mi, Z., et al., *J. Pharmacol. Exp. Ther.* 273: 728 (1995).
Gewirtz, H., et al.,*Proc. Soc. Exp. Bio. Med. 185*: 93 (1987).
Jackson, E.K., *Purinergic Approaches In Experimental Therapeutics*, Jacobson, K.A., et al., Ed. J. Wiley & Sons, NY pp. 217–50 (1997).
Adami, M. et al., *Eur. J. Pharmacol.* 294:383 (1985).
Yagil, Y., et al., *Am. J. Hyper.* 8: 509 (1995).
Iwamoto, T., et al., *Am. J. Hyper.* 7: 984 (1994).
Von Lubitz, D.K.J.E., et al., *Eur. J. Pharmacol.* 249: 271 (1993).

* cited by examiner

Primary Examiner—Theodore J. Criares
(74) Attorney, Agent, or Firm—Reed Smith LLP (57) ABSTRACT A method for preventing or treating gastrointestinal or systemic diseases in a mammalian subject, comprising:
  the step of administering a therapeutically effective amount of a composition comprising adenosine or a prodrug thereof into the peritoneal cavity of said subject at a dose that does not achieve pharmacologically active levels in the aortic arterial plasma of said subject.

7 Claims, 5 Drawing Sheets

Fig. 5D

INTRAPERITONEAL ADMINISTRATION OF ADENOSINE FOR THE TREATMENT OF PREVENTION OF GASTROINTESTINAL OF SYSTEMIC DISEASES

RELATED APPLICATIONS

This application claims priority from U.S. Provisional Application Serial No. 60/200,360 filed on Apr. 28, 2000.

FIELD OF INVENTION

The present invention relates generally to methods of treatment of gastrointestinal or systemic diseases. In particular, the present invention relates to methods of treatment or prevention of gastrointestinal or systemic diseases by administration of adenosine without causing adverse reactions.

BACKGROUND OF THE INVENTION

Adenosine has promise for the treatment or prevention of several bowel diseases. It is well known that adenosine has the ability to dilate the splanchnic circulation (see e.g., Proctor, K. G., *Circulation Res.* 59:474 (1986); Proctor, K. G., *Circulation Res.* 61:187 (1987); Jackson, E. K., *Am. J. Physiol.* 253:H909 (1987); Kuan, C. J., et al., *Am. J. Physiol.* 255:H386 (1988); and Holycross, B. J., et al., *J. Pharmacol. Exp. Ther.* 250:433 (1989) (hereinafter "Holycross, et al. (1989)"), the disclosures of which are incorporated herein by reference) inhibit platelet activation (see e.g., Dawicki, D. D., et al., *Thromb. Res.* 43:161 (1986); Paul, S., et al., *J. Pharmacol. Exp. Ther.* 267:838 (1993); and Cristalli, G., et al., *Naunyn-Schmiedebergs Archives of Pharmacology* 349:644 (1994), the disclosures of which are incorporated herein by reference) ; and attenuate neutrophil function (see e.g., Cronstein, B. N., *J. App. Phsiol.* 76:5 (1994) (hereinafter, "Cronstein (1994)"); Revan, S., et al., *J. Biol. Chem.* 271:17114 (1996); and Jordan, J. E., *J. Pharmacol. Exp. Ther.* 280:301 (1997), the disclosures of which are incorporated herein by reference). It has been further demonstrated that locally applied adenosine protects intestinal segments from ischemia/repercussion injury. See, Kaminski, P. M., et al., *Circulation Res.* 65:426 (1989) and Kaminski, P. M., et al., *Circulation Res.* 71:720 (1992), the disclosures of which are incorporated herein by reference. Adenosine may also be useful in the treatment of inflammatory diseases of the bowel such as Crohn's disease and ulcerative colitis because adenosine inhibits inflammatory cell function (Cronstein (1994)). It is also known that adenosine attenuates the production of inflammatory cytokines such as TNFα (Wagner, D. R., et al., *Circulation* 97:521 (1998); and Cain, B. S., et al., *J. Surg. Res.* 76:117 (1998), the disclosures of which are incorporated herein by reference). Moreover, adenosine inhibits fibroblast proliferation (Dubey, R. K., et al., *Circulation* 96:2656 (1997), the disclosure of which is incorporated herein by reference) extracellular matrix production by fibroblasts (Dubey, R. K., et al., *Hypertension* 31:943 (1998), the disclosure of which is incorporated herein by reference), and inflammation (Cronstein (1994)), all processes which are involved in the formation of intestinal adhesions (Klein, E. S., et al., *J. Surg. Res.* 61:473 (1996), the disclosure of which is incorporated herein by reference). The formation of intestinal adhesions is a major source of surgical morbidity (Thompson, J., *Digest. Surg.* 15:153 (1998), the disclosure of which is incorporated herein by reference).

The adverse effects of adenosine, however, limit the usefulness of this agent as a systemically (intravenously or intra-arterially) administered drug. When so administered, adenosine can cause heart block, asystole, arrhythmias, bradycardia, hypotension, bronchoconstriction and a stress reaction consisting of flushing, headache, dyspnea, chest pressure and nausea. It is therefore unlikely, given the adverse effect profile of adenosine and adenosine analogues, that systemic administration of these agents could be used to treat or prevent gastrointestinal diseases or most systemic diseases. Accordingly, the aim of the present invention is to determine whether adenosine could be administered in such a way that the beneficial effects of adenosine therapy may be taken advantage of to treat or prevent gastrointestinal or systemic diseases without attendant adverse effects.

SUMMARY OF THE INVENTION

Accordingly, it is a primary object of the present invention to provide a method of peritoneal lavage with adenosine which provides therapeutically effective levels of adenosine in the intestines of a subject without substantially elevating adenosine levels in the systemic circulation of the subject.

Another object of the present invention is to provide a method of peritoneal lavage with an adenosine-releasing "prodrug", i.e., a compound metabolized to adenosine, to provide pharmacological levels of adenosine in the intestines of a subject without elevating adenosine levels in the systemic circulation of the subject.

Still another object of the present invention is to provide a method of peritoneal lavage with adenosine -5'-monophosphate ("AMP"), an adenosine-releasing prodrug, to provide pharmacological levels of adenosine in the intestines of a subject without elevating adenosine levels in the systemic circulation of the subject.

Another object of the present invention is to provide a method of intraperitoneal administration of adenosine which confers therapeutic benefits, both locally and systemically, in a subject such as improved renal function, improved metabolic status, and improved survival in hemorrhagic shock.

These and other objects of the of the present invention are achieved by one or more of the following embodiments.

In one aspect, the invention features a method for preventing or treating gastrointestinal or systemic diseases in a mammalian subject, comprising:

the step of administering a therapeutically effective amount of a composition comprising adenosine or a prodrug thereof into the peritoneal cavity of the subject at a dose that does not achieve pharmacologically active levels in the aortic arterial plasma of the subject.

In preferred embodiments the phosphate ester of adenosine is selected from the group consisting of adenosine-5'-monophosphate, adenosine-5'-diphosphate, adenosine-5'-triphosphate, and adenosine 3':5'-cyclic monophosphate.

In another aspect, the invention features a pharmaceutical composition for treating gastrointestinal or inflammatory diseases in a mammalian subject, wherein the composition comprises adenosine or a prodrug thereof and a pharmaceutically acceptable carrier, and wherein the composition is administered into the peritoneal cavity of the subject at a therapeutically effective dose that does not achieve pharmacologically active levels in the aortic arterial plasma of the subject.

In yet another preferred embodiment, the phosphate ester of adenosine is selected from the group consisting of adenosine-5'-monophosphate, adenosine-5'-diphosphate, adenosine-5'-triphosphate, and adenosine 3':5'-cyclic monophosphate.

Other features and advantages of the invention will be apparent from the following description of the preferred embodiment, and from the claims.

DETAILED DESCRIPTION OF THE INVENTION

As used herein the term "peritoneal lavage" means placement of a solution into the peritoneal cavity of a subject. Peritoneal lavage may be carried out once, continuously, or intermittently, in accordance with the present invention.

"Mesenteric blood flow" refers to the volume of blood per unit time passing through the mesenteric artery.

"Mean arterial blood pressure" is the average (arithmetic mean) arterial blood pressure over a defined period of time.

A "prodrug of adenosine" means a compound that is metabolized or converted to adenosine such as, for example, adenosine-5'-monophosphate ("AMP"), adenosine-5'-diphosphate, adenosine-5'-triphosphate, and adenosine 3':5'-cyclic monophosphate.

"Pharmacologically active" refers to the level of adenosine that activates adenosine receptors in a subject.

"Splanchnic circulation" refers to circulation to the abdominal viscera of a subject.

Methods and Results

According to the present invention methods are provided for the treatment of diseases of the gastrointestinal tract as well as many systemic diseases. Specifically provided are methods for administering adenosine or a prodrug thereof to treat or prevent gastrointestinal or systemic diseases. According to the present invention, the adverse effects of adenosine that result from systemic administration (intravenous or intraarterial administration) are circumvented by administering adenosine or a prodrug thereof via single application or intermittent or continuous peritoneal lavage which induce beneficial effects on the intestines of a subject. This approach can achieve pharmacologically active levels of adenosine in the intestinal wall of a mammalian or human without producing significant levels of adenosine in the systemic circulation of the subject. However, there was a possibility that the metabolic barrier to adenosine absorption by the gastrointestinal tract, i.e., intestinal adenosine deaminase (see, Geiger, J. D., et al., *Adenosine and Adenine Nucleotides as Regulators of Cellular Function*, Phillis, J. W., Ed. CRC Press (1991), the disclosure of which is incorporated herein by reference), would be so effective in limiting the bioavailability of peritoneally administered adenosine that active levels of adenosine in the gastrointestinal tract could only be achieved with concentrations of adenosine in the peritoneal cavity so high that absorption at other sites in the peritoneal cavity would result in overwhelming systemic levels of adenosine. It was found that according to the present invention, however, that adenosine when administered to a subject by peritoneal lavage dilates the splanchnic circulation and increases adenosine levels in the mesenteric vein, without affecting systemic hemodynamics or increasing adenosine levels in the arterial circulation. The present invention therefore establishes that therapeutically effective levels of adenosine can be achieved in the peritoneal cavity in a subject without attaining pharmacologically active levels in the subject's systemic circulation.

The methods of the present invention are illustrated in more detail below. In one study, rats received an intramesenteric artery infusion of angiotensin II (30 μg/min) plus methoxamine (3 μg/min) to reduce mesenteric blood flow by approximately 60%, and adenosine solutions were instilled into the abdominal cavity. In a second study, microdialysis probes were placed in the mesenteric vein and aortic arch of rats, and the peritoneal cavity was continuously ravaged with adenosine or AMP solutions. In a third study, rats were subjected to hemorrhagic shock (2.75 ml of blood removed per 100 grams of body weight over a 15 minute period) for two hours, followed by volume resuscitation for one hour and observation for 72 hours. Rats received peritoneal lavage with adenosine or vehicle (0.9% saline) beginning 20 minutes after blood withdrawal and continuing through the one hour resuscitation period.

As will be seen, peritoneal lavage with adenosine normalized mesenteric blood flow (p<0.05) without affecting blood pressure or heart rate. Peritoneal administration of adenosine or AMP induced micromolar levels of adenosine and inosine in the mesenteric vein (p<0.05), without affecting adenosine or inosine levels in the aorta. Peritoneal lavage with adenosine increased survival in hemorrhagic shock (9 of 10 animals in the group treated with intraperitoneal adenosine survived for 72 hours, whereas only 4 of 10 animals in the group treated with vehicle survived for 72 hours; p<0.05). In rats subjected to hemorrhagic shock, intraperitoneal administration of adenosine significantly (p<0.05) improved metabolic parameters (reduced elevated plasma potassium and plasma lactate and increased arterial plasma pH) and improved renal function (reduced elevated blood urea nitrogen levels, an index of glomerular filtration rate). Therefore, according to the present invention, peritoneal lavage with adenosine or one of its prodrugs, AMP, provides pharmacological levels of adenosine in the gastrointestinal tract without systemic side effects. Peritoneal lavage with adenosine improves survival, metabolic status and renal function in hemorrhagic shock.

Peritoneal lavage with adenosine or adenosine prodrugs according to the present invention is useful for the treatment of a number of gastrointestinal and systemic diseases without the adverse effects associated with systemic administration of such drugs. Because adenosine increases gastrointestinal blood flow, peritoneal lavage with adenosine is useful to treat or prevent gastrointestinal diseases associated with inadequate blood flow to the intestines. Examples of such diseases are occlusion of mesenteric arterial or venous blood vessels caused by, for example, thrombosis or embolism of the mesenteric arteries or veins, atherosclerosis of the mesenteric arterial blood vessels, necrotizing enterocolitis, intestinal transplantation, traumatic injury to the intestines, or intestinal hypoperfusion due to hemorrhagic shock. Because adenosine is an antiinflammatory substance, peritoneal lavage with adenosine is useful to treat or prevent gastrointestinal diseases associated with inflammation of the bowel. Examples of such diseases include Crohn's disease, ulcerative colitis and reperfusion of the bowel following bowel ischemia for any reason and necrotizing enterocolitis. Because adenosine inhibits the proliferation of fibroblasts and the production of collagen by fibroblasts, peritoneal lavage with adenosine is useful to treat or prevent the formation of adhesions in the peritoneal cavity following abdominal surgery. Because adenosine inhibits the activity of various cells in the blood including platelets and neutrophils and because these blood cells circulate to the intestines, peritoneal lavage with adenosine is useful to treat or prevent systemic diseases in which activation of blood cells, particularly platelets and neutrophils, participate in the pathophysiology of the systemic disease. In this regard, adenosine in the intestinal circulation inhibits blood cells as they pass through the intestinal vasculature. Even though the adenosine is removed from the intestinal circulation as the blood draining the intestines passes through the intestines, liver and lungs, the inhibited blood cells remains inhibited for a period of time. Examples of diseases treatable or preventable by inhibiting blood cells with peritoneal adenosine include hemorrhagic shock, myocardial infarction and stroke.

Although this invention in its preferred embodiments is primarily addressed to use in humans, veterinary use is also anticipated and is encompassed by the present invention. In this regard, adenosine or a prodrug thereof may be administered intraperitoneally to dogs, cats, horses, cattle and sheep for gastrointestinal diseases such as, for example, preventing the formation of adhesions in the peritoneal cavity following surgery.

Adenosine or a prodrug thereof may be admixed with any pharmaceutically acceptable carrier or carriers, such as water, saline, physiological salt solutions, Ringer's solution, or any other carrier customarily used for intraperitoneal administration to the subject in question.

In that the method of the present invention involves administration of adenosine or a prodrug thereof intraperitoneally, the drug may be subject to destruction by adenosine deaminase or other enzymes. Therefore adenosine or a prodrug thereof accordingly must be administered in a larger concentration so that the amount is sufficient to achieve the desired therapeutic effect. The optimal therapeutic concentration of adenosine or adenosine prodrug in the peritoneal lavage solution will vary from species to species, individual to individual, and prodrug to prodrug depending on such factors as rate of uptake and metabolism of adenosine. For example, the rate of adenosine uptake is much higher in humans compared with rat red blood cells (Van Belle, H., *Biochim. Biophys. Acta* 192:124 (1969) and Jarvis, S. M., et al., *Biochem. J.* 208:83 (1982), the disclosures of which are incorporated herein by reference), and this may necessitate the use of even higher concentrations of adenosine or adenosine prodrugs in the peritoneal lavage solution to produce pharmacologically active concentrations of adenosine in the intestinal circulation in humans. On the other hand, some individuals may require less adenosine to deliver therapeutic amounts to the intestinal circulation and some prodrugs may be more or less efficient than adenosine in delivering appropriate amounts of adenosine to the intestinal circulation. It is within the skill of those in the art to determine the appropriate concentration of adenosine or prodrug thereof to be instilled into the peritoneal cavity of a subject.

The present invention will now be further illustrated by, but is by no means limited to, the following examples. It will be apparent to those skilled in the art that many modifications, both to materials and methods may be practical without departing from the purpose and interest of this invention.

In all the examples adult male Sprague-Dawley rats were purchased from Charles River Laboratories (Wilmington, Mass.) and maintained in the University of Pittsburgh Animal Facility (Pittsburgh, Pa.). Rats were provided free access to Prolab Isopro RMH 3000 rodent diet (PMI Nutrition Intl., Richmond, Ind.) and tap water. Light cycle, relative humidity and room temperature were 7:00 AM to 7:00 PM, 55% and 22° C., respectively. Animals weighed 357±11 (mean±SEM) grams at the time of study.

EXAMPLE 1

Rats were anesthetized with Inactin (100 mg/kg, i.p.) (Research Biochemicals International, Natick, Mass./Sigma, St. Louis, Mo.) and placed on a Deltaphase Isothermal Pad (Braintree Scientific, Inc.; Braintree, Mass). Body temperature was monitored with a digital rectal probe thermometer (Physiotemp Instruments, Inc.; Clifton, N.J.) and maintained at 37° C. by adjusting a heat lamp above the animal. The trachea was cannulated with polyethylene ("PE")-240 (Becton-Dickinson, Sparks, Md.) to maintain airway patency, a PE-50 catheter was inserted into the left jugular vein and an intravenous infusion of 0.9% saline was initiated at 50 $\mu$l/min. A left carotid artery catheter (PE-50) was inserted and was connected to a digital blood pressure analyzer (Micro-Med; Louisville, Ky.) for continuous measurement of mean arterial blood pressure (hereinafter "MABP") and heart rate. The digital blood pressure analyzer was set to time-average MABP and heart rate at two-minute intervals. A transit-time blood flow probe (Model 1RB; Transonic Systems Inc., Ithaca, N.Y.) was placed around the superior mesenteric artery and connected to a transit-time flowmeter (Model T206; Transonic Systems Inc.) to monitor mesenteric blood flow (hereinafter"MBF") continuously. A 32-gauge needle connected to a PE-1 inserted (proximal to the flow probe) into the superior mesenteric artery, and an intramesenteric artery infusion of 0.9% saline (50 $\mu$l/min) was then initiated. The animals were allowed to stabilize for approximately one hour after the surgical preparation was completed.

The abdominal skin and muscle flaps around the midline incision were supported in a bowl-shaped fashion to create a basin containing all the viscera, and 40 ml of 0.9% saline prewarmed to 37° C. was instilled into the peritoneal cavity. All abdominal viscera including the small and large intestines, pancreas, stomach, liver and spleen were submerged entirely in the peritoneal lavage fluid. MABP and heart rate were time-averaged (1100 Hz) over the last six minutes of the first 14-minute experimental period, and three readings of MBF were taken at two-minute intervals over the last six minutes of the first 14-minute experimental period and averaged.

Next, angiotensin II (30 μg/min) (Sigma) plus methoxamine (3 μg/min) (Sigma) were infused into the superior mesenteric artery (50 μl/min). This infusion was maintained for the duration of the experiment. After 20 minutes, the peritoneal lavage fluid was withdrawn and replaced with fresh, prewarmed saline. Again, MABP, heart rate and MBF were recorded as described above during the last six minutes of the second 14-minute experimental period. At this point, animals were assigned to one of three groups. In all groups, five additional back-to-back 14-minute experimental periods were conducted in which the peritoneal lavage fluid was removed and replaced at the beginning of each period and MABP, heart rate and MBF were recorded during the last six minutes of each period. In Group 1 (n=5), only fresh, prewarmed saline was instilled into the peritoneal cavity at the beginning of each experimental period. In Group 2 (n=5), increasing concentrations of adenosine ($10^{-7}$ M, $10^{-6}$ M, $10^{-5}$ M, $10^{-4}$ M and $10^{-3}$ M) dissolved in prewarmed saline were instilled into the peritoneal cavity at the beginning of each experimental period. In Group 3, $10^{-3}$ M adenosine was instilled into the peritoneal cavity at the beginning of each of the five remaining experimental periods.

Statistical Analysis: Data were analyzed in this example by repeated measures 1-factor analysis of variance. If the analysis of variance demonstrated a significant effect of the treatments, post-hoc comparisons were calculated with a Fisher's Least Significant Difference ("LSD") test. Statistical analyses were conducted with NCSS software (Version 6.0; Kaysville, Utah), and the criterion of significance was p<0.05.

EXAMPLE 2

Rats (n=5) were anesthetized and body temperature monitored and maintained as described for Example 1. The trachea was cannulated with PE-240 and a PE-50 catheter was inserted into the right jugular vein and an intravenous infusion of 0.9% saline was initiated at 50 μl/min. A femoral artery catheter (PE-50) was inserted and was connected to a digital blood pressure analyzer for continuous measurement of MABP and heart rate. Next, microdialysis probes (CMA/20 microdialysis probe 4 mm, Bioanalytical Systems, Inc., West Lafayette, Ind.) were inserted into the aortic arch (via the left carotid artery) and mesenteric vein. Microdialysis probes were perfused with 0.9% saline at 2 μl/min, and the dialysate exiting the probes was collected in a freezing apparatus. As in Example 1, a basin was constructed from the abdominal wall to create a bowl containing the viscera. However, unlike Example 1, instead of intermittent lavage with fresh solutions, the abdominal basin was continuously perfused with Tyrode's solution (5 ml/min) (Mi, Z., et al., *J. Pharmacol. Exp. Ther.* 287:926 (1998), the disclosure of which is incorporated herein by reference) that was maintained at 37° C. by a heated water bath. Thus, the viscera were submerged completely in Tyrode's solution that was constantly being replaced. After a 20-minute stabilization period, dialysate from the microdialysis probes was collected for 20 minutes. Next, the Tyrode's solution perfusing the peritoneal cavity was switched to prewarmed Tyrode's containing $10^{-5}$ M adenosine (Sigma). After 10 minutes, the dialysate was collected for another 20 minutes. This procedure was repeated two more times as the concentration of adenosine was increased to $10^{-4}$ M and finally to $10^{-3}$ M. To determine whether AMP would behave as a "prodrug" for the delivery of adenosine, after a 20 minute washout period, the entire protocol was repeated with AMP ($10^{-5}$ M, $10^{-4}$ M and $10^{-3}$ M) (Sigma).

Statistical Analysis: Data were analyzed in this example by repeated measures 1-factor analysis of variance. If the analysis of variance demonstrated a significant effect of the treatments, post-hoc comparisons were calculated with a Fisher's Least Significant Difference ("LSD") test. Statistical analyses were conducted with NCSS software (Version 6.0; Kaysville, Utah), and the criterion of significance was p<0.05.

Sample Analysis: Levels of adenosine and its metabolites, inosine, hypoxanthine and xanthine, in the dialysate samples in this example were measured using an Isco (Lincoln, Nebr.) high-pressure liquid chromatographic system (pump model 2350, gradient programmer model 2360, 4.6×250-mm $C_{18}$ column) with UV detection as described by Mi, Z., et al., *J. Pharmacol. Exp. Ther.* 273:728 (1995). The chromatography data system was JCL 6000 for Windows (Jones Chromatography LTD., Lakewood, Colo.).

EXAMPLE 3

Rats were anesthetized and instrumented with venous and arterial catheters for blood withdrawal, infusions and monitoring of heart rate and MABP. Hemorrhagic shock was induced by removing 2.75 ml of blood per 100 grams of body weight over a 15 minute period. Two hours after blood withdrawal, the animals were resuscitated by reinfusing the withdrawn blood and restoring and maintaining a normal blood pressure for one hour by infusing Ringer's solution (Baxter, Deerfield, Ill.) as needed. Beginning 20 minutes after blood withdrawal and continuing for one hour after reinfusion of the withdrawn blood, rats received either continuous peritoneal lavage with adenosine ($10^{-4}$ M) or 0.90% saline.

Results

Figure 1A:
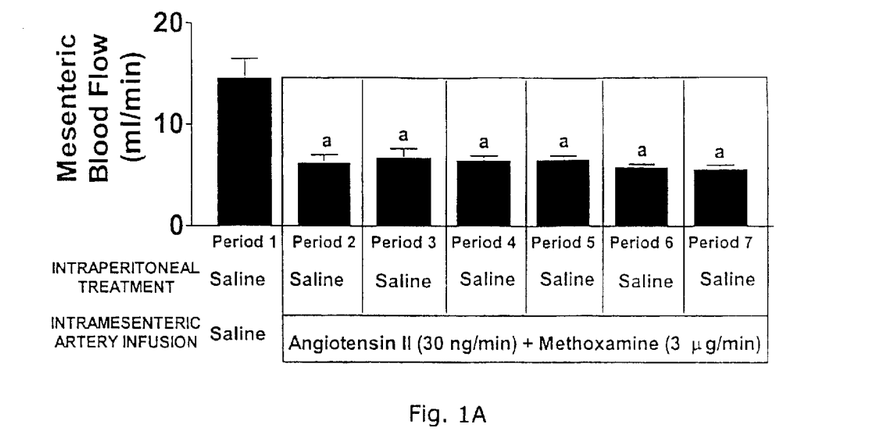
FIGS. 1A–1C show mesenteric blood flow before (Period 1) and during (Periods 2–7) an intramesenteric artery infusion of angiotensin II plus methoxamine in three groups of rats (n=5 per group). Rats received intermittent intraperitoneal lavage with 0.9% saline only (FIG. 1A), increasing concentrations of adenosine ("ADO") (FIG. 1B), or a fixed high concentration of adenosine (FIG. 1C), respectively. Values represent means±SEM. $^a$p<0.05 compared with Period 1; $^b$p<0.05 compared with Period 2.
Figure 1B:
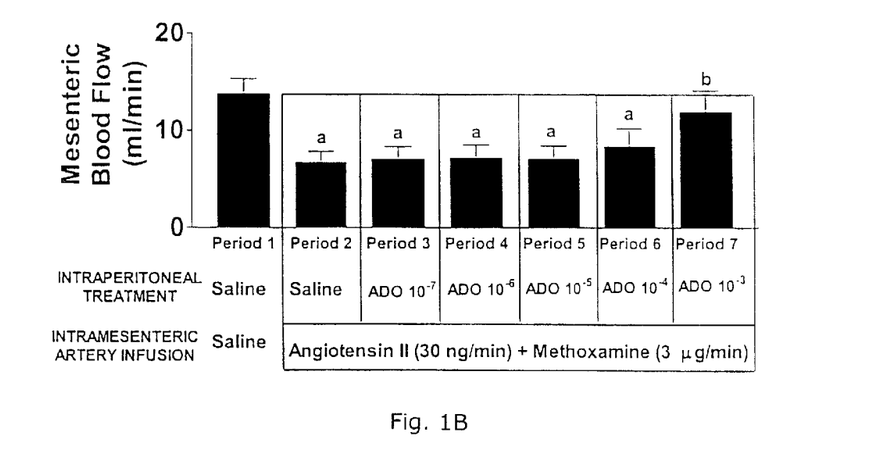

Example 1: Basal MBFs were similar in the three groups (14.5±2.0, 13.8±1.5 and 14.8±1.7 ml/min in Groups 1, 2 and 3, respectively). Intramesenteric artery infusions of angiotensin II (30 ng/min) plus methoxamine (3 μg/min) caused an immediate decrease in MBF during experimental period 2 such that MBFs in the three groups were 6.2±0.8, 6.6±1.2 and 6.1±1.0 ml/min in Groups 1, 2 and 3, respectively. As illustrated in FIG. 1A, in Group 1 (the time-vehicle control group) MBF remained depressed throughout the six experimental periods (periods 2 through 7) during the intramesenteric infusions of angiotensin II plus methoxamine. In Group 2, MBF remained significantly depressed and similar in experimental periods 2 through 6 when the adenosine concentration in the peritoneal lavage fluid was 0, $10^{-7}$ M, $10^{-6}$ M, $10^{-5}$ M and $10^{-4}$ M, respectively. However, during the final experimental period (period 7) when the concentration of adenosine in the peritoneal lavage fluid was $10^{-3}$ M (FIG. 1B), MBF increased. In this regard, the MBF during period 7 was significantly greater than the MBF during period 2 (intramesenteric artery infusion of angiotensin II plus methoxamine but no adenosine in the peritoneal lavage fluid) but not significantly different than the MBF during period 1 (no intramesenteric infusion and no adenosine in the peritoneal lavage fluid).

Figure 1C:
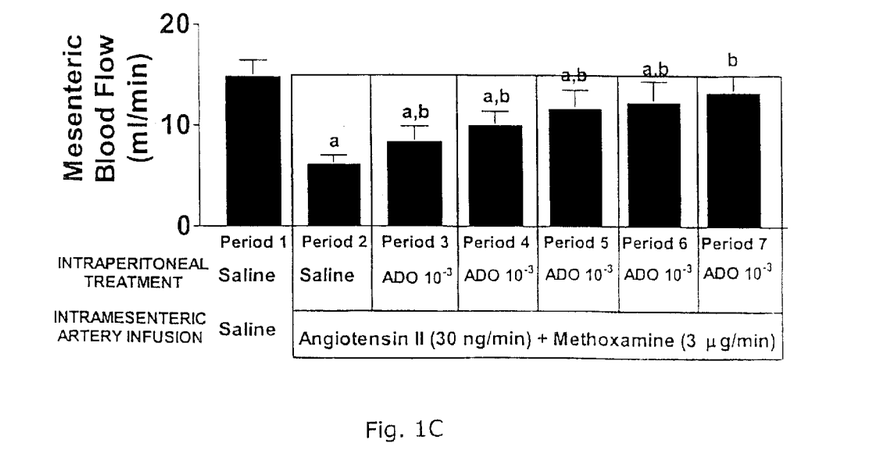
Figure 2A:
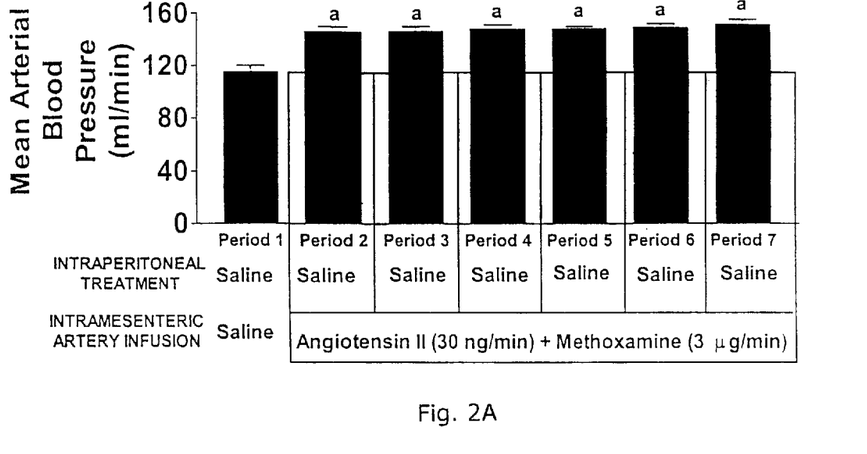
FIGS. 2A–2C show mean arterial blood pressure before (Period 1) and during (Periods 2–7) an intramesenteric artery infusion of angiotensin II plus methoxamine in three groups of rats (n=5 per group). Rats received intermittent intraperitoneal lavage with 0.9% saline only (FIG. 2A), increasing concentrations of adenosine ("ADO") (FIG. 2B), or a fixed high concentration of adenosine (FIG. 2C), respectively. Values represent means±SEM. $^a$p<0.05 compared with Period 1; $^b$p<0.05 compared with Period 2.
Figure 2B:
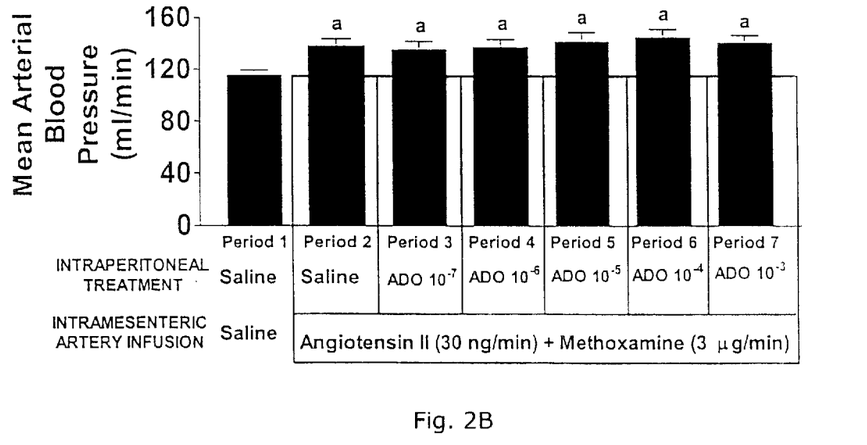
Figure 2C:
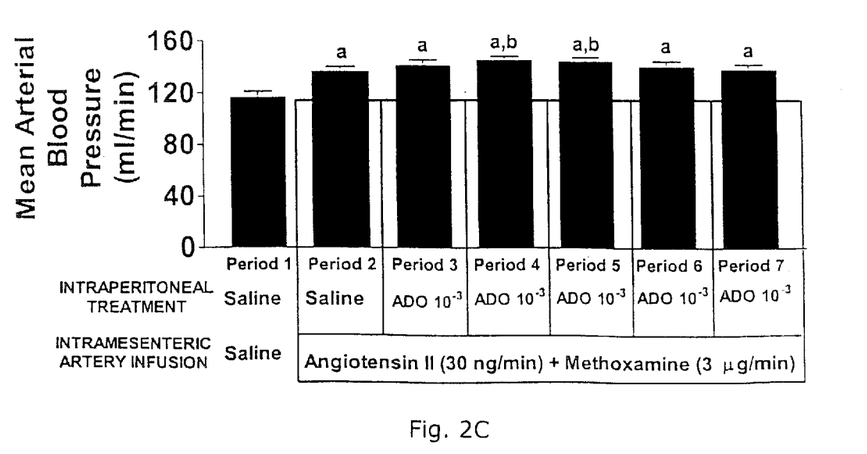

FIG. 1C illustrates the effects of $10^{-3}$ M adenosine in the peritoneal lavage fluid added during experimental periods 3 through 7. This high concentration of adenosine caused an immediate increase in MBF such that MBF during experimental periods 3 through 7 were significantly greater than MBF during period 2. Also, by period 7, MBF had increased to the point that it was no longer significantly different compared with experimental period 1.

Figure 3A:
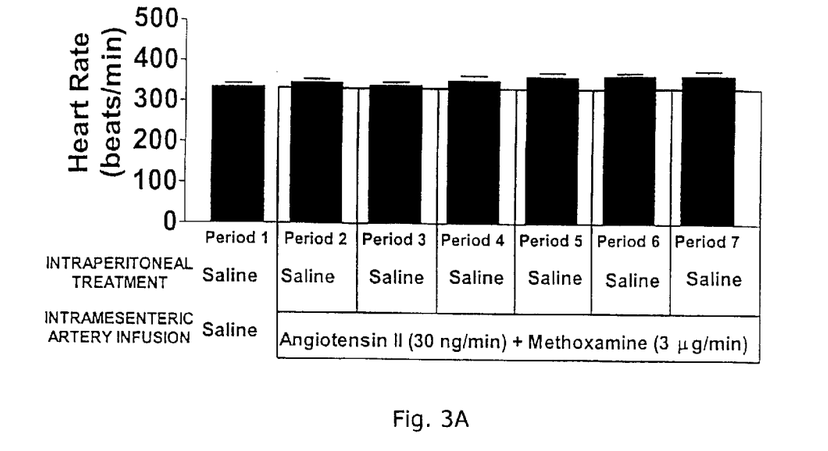
FIGS. 3A–3C show heart rate before Period 1) and during (Periods 2–7) an intramesenteric artery infusion of angiotension II plus methoxamine in three groups of rats (n=5 per group). Rats received intermittent intraperitoneal lavage with 0.9% saline only (FIG. 3A), increasing concentrations of adenosine ("ADO") (FIG. 3B), or a fixed high concentration of adenosine (FIG. 3C), respectively. Values represent means±SEM. $^a$p<0.05 compared with Period 1; $^b$p<0.05 compared with Period 2.
Figure 3B:
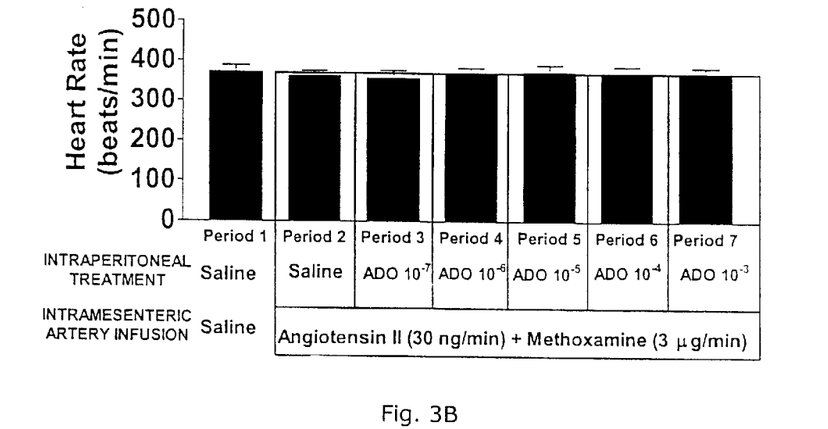
Figure 3C:
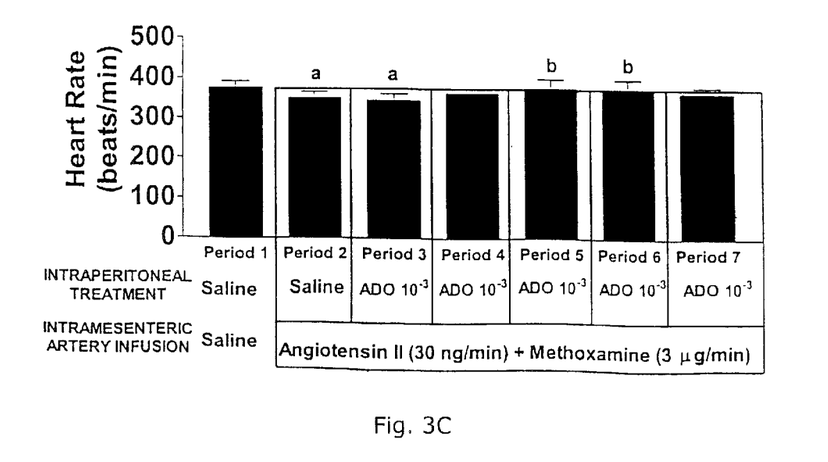
Figure 4A:
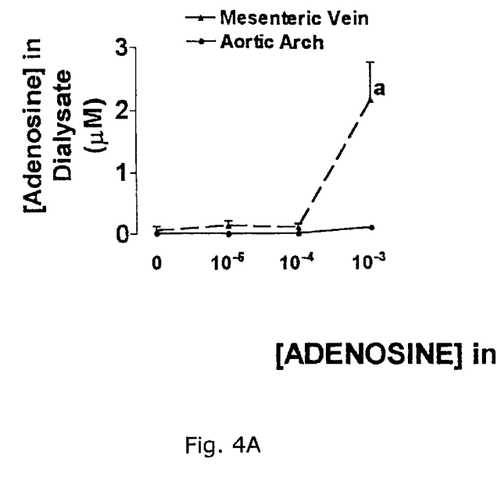
FIGS. 4A–4D show concentrations of adenosine (FIG. 4A), and its metabolites, inosine (FIG. 4B), hypoxanthine (FIG. 4C) and xanthine (FIG. 4D), in the dialysate exiting the microdialysis probe in the mesenteric vein and aortic arch during continuous peritoneal lavage with adenosine. Values represent means±SEM (n=5). $^a$p<0.05 compared with all other points.
Figure 4B:
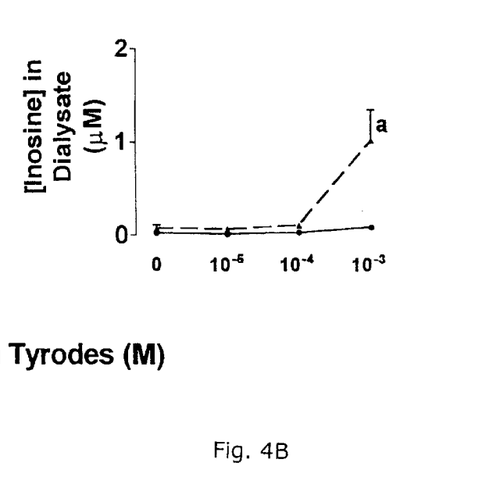
Figure 4C:
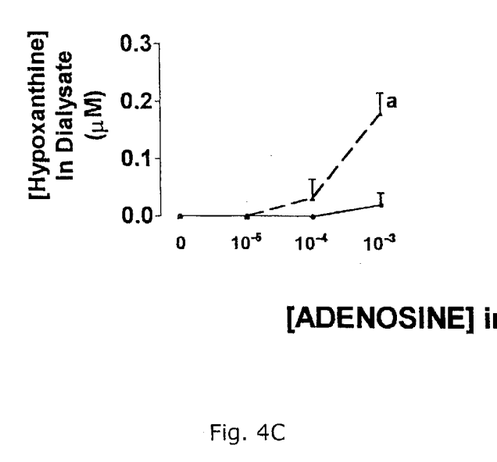
Figure 4D:
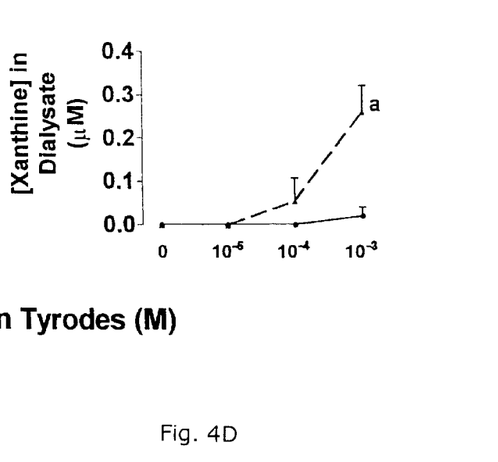
Figure 5A:
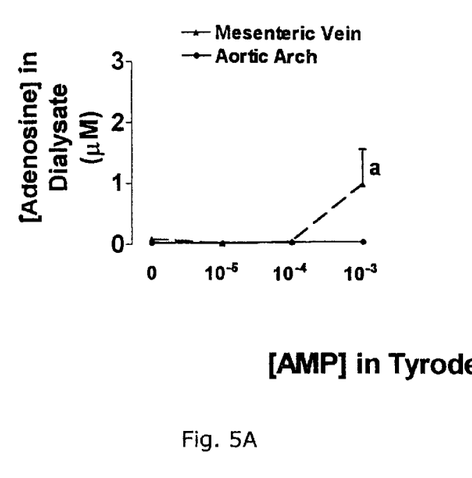
FIGS. 5A–5D show concentrations of adenosine (FIG. 5A) and its metabolites, inosine (FIG. 5B), hypoxanthine (FIG. 5C), and xanthine (FIG. 5D) in the dialysate exiting the microdialysis probe in the mesenteric vein and aortic arch during continuous peritoneal lavage with AMP. Values represent means±SEM (n=5). $^a$p<0.05 compared with all other points.
Figure 5B:
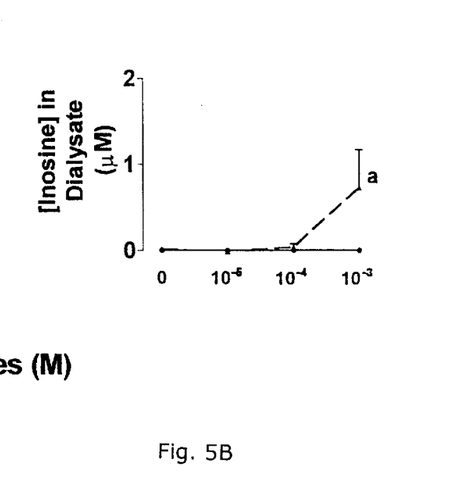
Figure 5C:
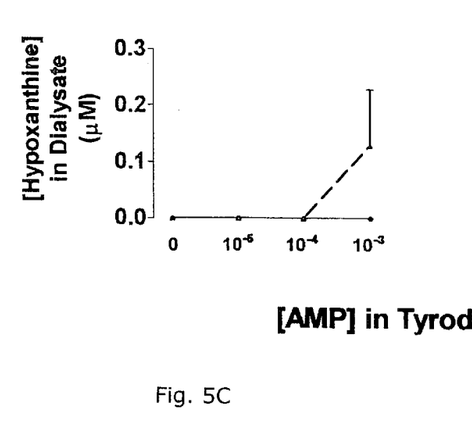
Figure 5D:
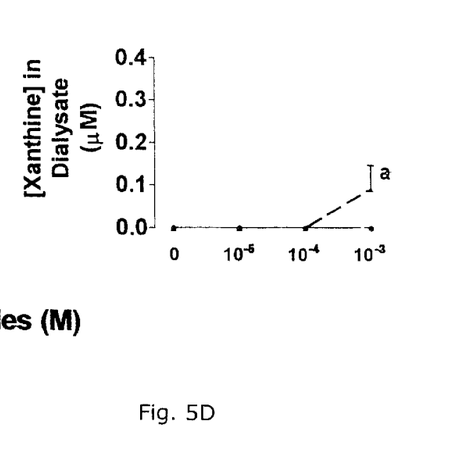

FIGS. 2A–2C and FIGS. 3A–3C summarize the MABP and heart rate, respectively, in the three groups of rats. With regard to MABP, the intramesenteric infusion of angiotensin II and methoxamine caused a marked increase in MABP from period 1 to period 2 (Group 1: 115±5 to 146±4 mm Hg; Group 2: 115±4 to 138±6 mm Hg; Group 3: 117±5 to 136±4 mm Hg). In all three groups this hypertensive effect of angiotensin II plus methoxamine was maintained throughout experimental periods 2–7 and was not decreased by peritoneal lavage with adenosine. As shown in FIGS. 3A–3C in Groups 1 and 2, heart rate was not significantly different among the seven experimental periods. In Group 3, angiotensin II plus methoxamine caused a slight, but significant, decrease in heart rate during periods 2 and 3; however this effect faded during the subsequent experimental periods. In Group 3, the high concentration of adenosine in the peritoneal lavage fluid did not cause bradycardia, the typical response to intravenous adenosine in the anesthetized rat (Holycross et al. (1989)).

Example 2: Basal levels of adenosine, and its metabolites, inosine, hypoxanthine and xanthine, in the dialysate from the mesenteric vein and aorta were less than 0.1 $\mu$M. As shown in FIGS. 4A–4D, continuous lavage of the peritoneal cavity with either $10^{-5}$ M, $10^{-4}$ M or $10^{-3}$ M adenosine did not significantly alter the levels of adenosine, inosine, hypoxanthine or xanthine in the aorta. Likewise, continuous lavage of the peritoneal cavity with either $10^{-5}$ M or $10^{-4}$ M adenosine did not significantly alter the levels of adenosine, inosine, hypoxanthine or xanthine in the mesenteric vein. However, continuous lavage of the peritoneal cavity with $10^{-3}$ M adenosine increased markedly and significantly the levels of adenosine (2.17±0.60 $\mu$M), inosine (1.03±0.32 $\mu$M), hypoxanthine (0.18±0.04 $\mu$M ) and xanthine (0.26±0.06 $\mu$M) in the dialysate exiting the mesenteric vein microdialysis catheter. Like adenosine, $10^{-3}$ M AMP also increased purine levels in the mesenteric vein, but not in the aorta (FIGS. 5A–5D). The increase in mesenteric venous levels of adenosine with $10^{-3}$ M AMP tended to be less compared with the increase induced by $10^{-3}$ M adenosine (1.02±0.57 and 2.17±0.60 $\mu$M, respectively); however, this difference was not statistically significant. Neither adenosine nor AMP significantly affected MABP (113±5 versus 108±4 mm Hg, basal and during $10^{-3}$ M adenosine, respectively; 112±4 versus 117±7 mm Hg, basal and during $10^{-3}$ M AMP, respectively) or heart rate (351±15 versus 362±14 beats/min, basal and during $10^{-3}$ M adenosine, respectively; 357±17 versus 366±22 beats/min, basal and during $10^{-3}$ M AMP, respectively).

Example 3: MABP and heart rate were similar between the adenosine-treated and vehicle-treated groups during hemorrhagic shock and resuscitation. Plasma levels of potassium, lactate and blood urea nitrogen were significantly ($p<0.05$) lower and arterial pH was significantly ($p<0.05$) higher in the adenosine-treated group compared with the vehicle-treated group. Survival to 72 hours was significantly ($p<0.05$) greater in the adenosine-treated group (9 of 10 animals) compared with the vehicle-treated group (4 of 10 animals).

Discussion

The present invention is directed to peritoneal administration of adenosine to provide therapeutically active levels of adenosine in the intestines without inducing pharmacologically active levels of adenosine in the systemic circulation. The methods were tested in two separate protocols.

The logic of the first protocol was to induce severe vasoconstriction in the mesenteric circulation with an intramesenteric artery infusion of angiotensin II plus methoxamine ($\alpha_1$-adrenoceptor agonist) so that the direct vasodilatory effects of adenosine on the splanchnic circulation could serve as an index of pharmacologically active levels of adenosine in the intestines. Importantly, the intramesenteric artery infusion of angiotensin II plus methoxamine effectively reduced MBF in all three groups of animals. Equally important, the effect of angiotensin II plus methoxamine on MBF was maintained in the time-control animals, thus indicating that any increase in MBF in the adenosine-treated animals could be interpreted as an effect of the adenosine and not tachyphylaxis to the vasoconstrictors.

In the animals that received intermittent peritoneal lavage with increasing concentrations of adenosine, low concentrations of adenosine did not affect MBF. This indicates that the metabolic barrier of the intestines to adenosine bioavailability is large, i.e., it is difficult for intact molecules of adenosine to be absorbed, avoid metabolism and gain entry into the splanchnic circulation. However, despite the low bioavailability of intraperitoneal adenosine, when the concentration of adenosine was increased, active levels of adenosine were achieved in the splanchnic circulation as evidenced by the marked increase in MBF. This finding was confirmed in the third group of rats in which a high concentration of adenosine was added to the peritoneal lavage beginning in period 3 and continuing through period 7. In this latter group, adenosine rapidly increased MBF, and MBF continued to increase over the ensuing periods.

Since in the anesthetized rat adenosine causes profound bradycardia and hypotension, heart rate and arterial blood pressure were used to monitor for the presence of pharmacologically active levels of adenosine in the system circulation. The intramesenteric artery infusion of angiotensin II plus methoxamine increased MABP, most likely due to spillover of the infused pressor agents to the systemic circulation. This pressor effect was fortuitous since it provided an increased MABP upon which to assess adenosine-induced decreases in blood pressure. As with MBF, the systemic pressor response to angiotensin II plus methoxamine was maintained at a constant level in the time-control animals, thus making any changes observed in the adenosine-treated animals interpretable.

In Group 2, the group treated with increasing concentrations of adenosine, adenosine did not cause a reduction in arterial blood pressure regardless of the concentration instilled into the peritoneal cavity. Likewise, when a high concentration of adenosine was instilled into the peritoneal cavity during period 3 and maintained through period 7, MABP was not decreased. In this latter group, there was a very slight and transient increase in MABP during period 4 and period 5 but this was unlikely due to a direct effect of adenosine on the systemic circulation since adenosine decreases, rather than increases, arterial blood pressure in anesthetized rats (Holycross, et al. (1989)). Thus, the MABP data indicate that even extremely high concentrations of adenosine added to the peritoneal cavity do not result in pharmacologically active levels of adenosine in the systemic circulation. This is an important finding because it indicates that absorption of adenosine from the surface of other organs (pancreas, spleen, liver, stomach) and the abdominal walls does not result in systemically active levels of adenosine despite the presence of extremely high levels of adenosine in the peritoneal lavage fluid.

The inference from the MABP data that adenosine in the peritoneal lavage fluid does not reach the systemic circulation in any appreciable amounts is supported further by the heart rate data. Since adenosine in the anesthetized rat causes profound bradycardia (Holycross, et al. (1989)), the inability of adenosine in the peritoneal lavage fluid to decrease heart rate adds weight to the conclusion that adenosine placed in the peritoneal cavity does not reach the systemic circulation in active amounts.

The first example employed a "bioassay" to test the hypothesis that peritoneal lavage with adenosine would result in pharmacological levels of adenosine in the intestines without inducing pharmacological levels of adenosine in the systemic circulation. However, it is always preferable to address the same question using more than one approach. In the second study, microdialysis probes were placed in the mesenteric vein and aortic arch to measure more directly whether or not adenosine in the lavage fluid gains access to the splanchnic circulation and/or the systemic circulation. Microdialysis, rather than direct blood sampling, was selected for measurement of adenosine levels because of the multiple problems of adenosine uptake and metabolism by formed elements in the blood, as well as the problem of ex vivo generation of adenosine in the sampled blood due to release of ADP from damaged red blood cells (Gewirtz, H., et al., *Proc. Soc. Exp. Bio. Med.* 185:93 (1987), the disclosure of which is incorporated herein by reference). Although absolute levels of purines in the dialysate cannot necessarily be equated with plasma levels of adenosine, changes in dialysate levels of purines would reflect changes in plasma levels of purines.

Importantly, no concentration of adenosine in the peritoneal lavage fluid caused any significant increase in adenosine levels or adenosine metabolite (inosine, hypoxanthine, xanthine) levels in the systemic circulation. This firmly supports the conclusion from the first example that adenosine placed in the peritoneal cavity does not generate pharmacologically active levels of adenosine in the systemic circulation. Also in line with the first example, high concentrations of adenosine in the peritoneal cavity cause marked and significant increases in adenosine and adenosine metabolite levels in the mesenteric vein.

Taken together, the data indicate that although the intestinal barrier to adenosine bioavailability is great, this barrier can be overcome with high concentrations of adenosine. Moreover, the data indicate that regardless of the concentration of adenosine in the peritoneal lavage fluid, levels of adenosine in the systemic circulation remain low and below the threshold for biological effects. The data indicate that peritoneally administered adenosine (either by single administration or intermittent lavage or continuous lavage) could be used to treat intestinal diseases. Disease candidates for this method include disorders leading to bowel ischemic injury, reperfusion injury, inflammation or, adhesion formation. In the present invention, the utility of intraperitoneal administration of adenosine for hemorrhagic shock, a disease characterized by organ (including the gut) ischemic injury and reperfusion injury is demonstrated. In this regard, peritoneal administration of adenosine improved metabolic status, renal function and survival in animals that were subjected to two hours of hemorrhagic shock.

Peritoneal adenosine also can be used to inhibit circulating inflammatory cells without systemic side effects. In this regard, blood flow through the splanchnic circulation would deliver inflammatory cells, such as neutrophils, to the gut where peritoneally administered adenosine could activate adenosine receptors on the inflammatory cells to alter their behavior. Although the altered inflammatory cells would travel back to the systemic circulation, the adenosine that altered them would not. Thus, peritoneally administered adenosine would be useful for diseases of other organ systems, including the heart, lungs, kidneys and brain, in which inflammation plays a significant role. This explains in part the benefit of peritoneally administered adenosine in hemorrhagic shock.

Like adenosine, high concentrations of AMP also significantly increased adenosine levels in the mesenteric vein without increasing adenosine levels in the aorta. Since AMP is efficiently metabolized to adenosine by ecto-5'-nucleotidase (an enzyme found widely in the body including the gut), AMP functions as a "prodrug" that is readily converted to adenosine. Thus, peritoneal lavage with adenosine prodrugs (examples, AMP, adenosine-5'-diphosphate, adenosine-5'-triphosphate and adenosine 3':5'-cylic monophosphate) can also be used for treating the aforementioned diseases.

A potential concern regarding the intraperitoneal administration of adenosine is the release of histamine from mast cells, a process that can contribute to adenosine-mediated hypotension. However, the inability of adenosine in the peritoneal lavage fluid to decrease MABP rules out the release of significant amounts of systemically bioavailable histamine from mast cells by intraperitoneal adenosine. Another concern is the effects of adenosine on the kidneys. In this regard, adenosine causes renal vasoconstriction (Jackson, E. K., *Purinergic Approaches In Experimental Therapeutics,* Jacobson, K. A., et al., Ed. J. Wiley & Sons, NY. pp. 217-50 (1997), the disclosure of which is incorporated herein by reference). However, the kidneys are retroperitoneal organs, so adenosine applied in the peritoneal cavity would not have access to the renal circulation.

It is unlikely that "chronic" administration of adenosine by peritoneal lavage would induce significant toxicity. This hypothesis is based on three lines of reasoning. First, since systemic concentrations of adenosine are low during acute peritoneal lavage with high concentrations of adenosine, it is likely that systemic concentrations of adenosine also would be low during more prolonged administration of peritoneal adenosine. This would limit toxicity during chronic administration of adenosine by the peritoneal route. Second, the definition of "chronic" administration in the context of peritoneal lavage with adenosine for therapeutic applications would most likely be only a few days or weeks. This too would limit the likelihood of systemic or local toxicity. Third, although the literature is sparse with regard to chronic administration of adenosine analogues by the oral or peritoneal route, the published articles to date do not mention toxicity. In this regard, Adami, M., et al., *Eur. J. Pharmacol.* 294:383 (1985), the disclosure of which is incorporated herein by reference, administered either 2-chloro-$N^6$-cyclopentyladenosine (adenosine $A_1$ receptor agonist), 2-hexynyl-5'-N-ethylcarboxamidoadenosine (adenosine $A_2$ receptor agonist), or 5'-N-ethylcarboamidoadenosine (nonselective adenosine receptor agonist) to rats intraperitoneally twice daily for 12 days at doses that protected 50% of animals from pentylenetetrazole-induced lethal seizures. Yagil, Y., et al., *Am. J. Hyper.* 8:509 (1995), the disclosure of which is incorporated herein by reference, administered 6-(O-methylbenzyl) adenosine (adenosine $A_2$ receptor agonist) to rats daily by the oral route for 5 days at hypotensive doses. Iwamoto, T., et al., *Am. J. Hyper.* 7:984 (1994), the disclosure of which is incorporated herein by reference, gave 2-octynyl adenosine (adenosine $A_2$ receptor agonist) to rats daily by the oral route for 10 days at hypotensive doses. Finally, Von Lubitz, D. K. J. E., et al., *Eur. J. Pharmacol.* 249: 271 (1993), the disclosure of which is incorporated herein by reference, administered $N^6$-cyclopentyladenosine (adenosine $A_1$ receptor agonist) to mice intraperitoneally once daily for 9 days at doses that increased spatial memory acquisition in the Morris water maze test. It is important to note that in the aforementioned studies, metabolically stable adenosine analogues were used that readily escape adenosine clearance mechanisms in the intestines, liver and lungs. In these studies, pharmacologically active concentrations of adenosine analogues reached the systemic circulation. Thus, the aforementioned studies differ importantly from the present invention in which pharmacologically active levels of adenosine were not induced by intraperitoneally administered adenosine or adenosine prodrug.

In conclusion, the present invention demonstrates that pharmacologically active concentrations of adenosine can be obtained in the gut circulation by administering adenosine or AMP into the peritoneal cavity. Moreover, it has been established that administration of even very high concentrations of adenosine or an adenosine prodrug into the peritoneal cavity does not increase adenosine levels in the systemic circulation. Thus, intraperitoneal administration of adenosine or adenosine prodrugs will be useful for the treatment of a number of gastrointestinal or systemic diseases.

Although the invention has been described in detail for the purposes of illustration, it is to be understood that such detail is solely for that purpose and that variations can be made therein by those skilled in the art without departing from the spirit and scope of the invention except as it may be limited by the claims.

I claim:

1. A method for preventing or treating gastrointestinal or systemic diseases in a mammalian subject, comprising:

the step of administering a therapeutically effective amount of a composition comprising adenosine or a prodrug thereof into the peritoneal cavity of said subject at a dose that does not achieve pharmacologically active levels in the aortic arterial plasma of said subject.

2. The method of claim 1, wherein said adenosine prodrug is an ester of adenosine.

3. The method of claim 2, wherein said ester of adenosine is a phosphate ester of adenosine.

4. The method of claim 3, wherein said phosphate ester of adenosine is selected from the group consisting of adenosine-5'-monophosphate, adenosine-5'-diphosphate, adenosine-5'-triphosphate, and adenosine 3':5'-cyclic monophosphate.

5. The method of claim 1, wherein said mammalian subject is a human.

6. The method of claim 1, wherein said disease is formation of adhesions in the peritoneal cavity of said subject during or following abdominal surgery.

7. The method of claim 1, wherein said adenosine prodrug is a composition that releases adenosine.

* * * * *

UNITED STATES PATENT AND TRADEMARK OFFICE
CERTIFICATE OF CORRECTION

PATENT NO.    : 6,566,371 B2                                            Page 1 of 1
DATED         : May 20, 2003
INVENTOR(S)   : Jackson It is certified that error appears in the above-identified patent and that said Letters Patent is hereby corrected as shown below:

<u>Title page, Item [54] and Column 1, lines 2 and 3,</u>
Title, after "TREATMENT" delete "OF" and substitute -- OR -- therefor; and after "GASTROINTESTINAL" delete "OF" and substitute -- OR -- therefor.

Signed and Sealed this

Fifteenth Day of July, 2003

JAMES E. ROGAN
*Director of the United States Patent and Trademark Office*